(12) United States Patent  
Shiuey

(10) Patent No.: US 7,223,275 B2
(45) Date of Patent: May 29, 2007

(54) SYSTEM FOR CUTTING THE CORNEA OF AN EYE

(76) Inventor: Yichieh Shiuey, 1129 Cabot Pl., San Jose, CA (US) 95129

( * ) Notice: Subject to any disclaimer, the term of this patent is extended or adjusted under 35 U.S.C. 154(b) by 420 days.

(21) Appl. No.: 10/445,065

(22) Filed: May 27, 2003

(65) Prior Publication Data

US 2004/0243159 A1 Dec. 2, 2004

(51) Int. Cl.
*A61F 9/00* (2006.01)
(52) U.S. Cl. .................. 606/166; 606/161; 606/167; 606/107
(58) Field of Classification Search ........... 606/161, 606/166, 167, 107
See application file for complete search history.

(56) References Cited

U.S. PATENT DOCUMENTS

| | | | |
|---|---|---|---|
| 4,655,774 A * | 4/1987 | Choyce | 623/5.11 |
| 5,215,104 A * | 6/1993 | Steinert | 128/898 |
| 5,624,456 A * | 4/1997 | Hellenkamp | 606/166 |
| 5,779,723 A | 7/1998 | Schwind | |
| 5,807,380 A | 9/1998 | Dishler | |
| 5,944,731 A | 8/1999 | Hanna | |
| 5,964,776 A | 10/1999 | Peyman | |
| 6,022,365 A | 2/2000 | Aufaure et al. | |
| 6,045,562 A | 4/2000 | Amano et al. | |
| 6,045,563 A | 4/2000 | Duprat | |
| 6,083,236 A | 7/2000 | Feingold | |
| 6,126,668 A | 10/2000 | Blair et al. | |
| 6,139,560 A * | 10/2000 | Kremer | 606/166 |
| 6,183,488 B1 * | 2/2001 | Ross et al. | 606/166 |
| 6,228,099 B1 | 5/2001 | Dybbs | |
| 6,277,134 B1 | 8/2001 | Amano et al. | |
| 6,296,650 B1 | 10/2001 | Carriazo | |
| 6,325,792 B1 * | 12/2001 | Swinger et al. | 606/4 |
| 6,332,890 B1 | 12/2001 | Ortega et al. | |
| 6,344,046 B2 * | 2/2002 | Sugimura et al. | 606/166 |
| 6,358,260 B1 | 3/2002 | Ross et al. | |
| 6,599,305 B1 * | 7/2003 | Feingold | 606/166 |
| 2001/0004702 A1 * | 6/2001 | Peyman | 606/166 |
| 2001/0053917 A1 * | 12/2001 | Lin et al. | 606/166 |
| 2002/0045910 A1 * | 4/2002 | Aufaure et al. | 606/166 |
| 2002/0091401 A1 * | 7/2002 | Hellenkamp | 606/166 |

* cited by examiner

*Primary Examiner*—Corrine McDermott
*Assistant Examiner*—Christopher D. Prone
(74) *Attorney, Agent, or Firm*—Townsend and Townsend and Crew LLP

(57) ABSTRACT

A system for cutting the cornea of an eye includes a moveable member with a cutting blade at one end, a pivot element disposed thereon, a cutting guide restraint disposed thereon, a mechanism for oscillating the moveable member around the pivot element, and a cutting guide configured to engage the cutting guide restraint on the moveable member to thereby limit the degree of angular movement of the cutting blade as the moveable member oscillates about the pivot element. A pocket can be cut in the cornea by advancing and oscillating the moveable member.

11 Claims, 8 Drawing Sheets

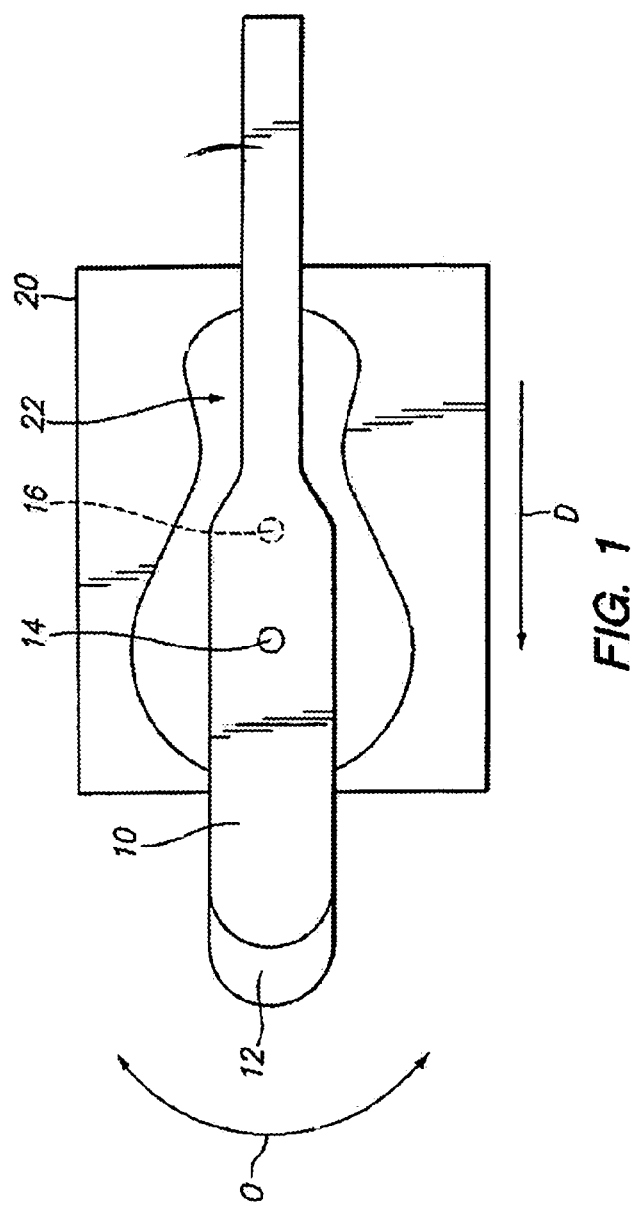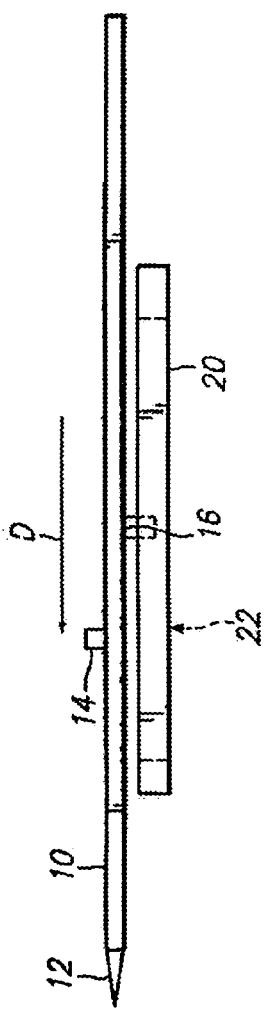

SYSTEM FOR CUTTING THE CORNEA OF AN EYE

TECHNICAL FIELD

The present invention relates to surgical systems for cutting the cornea of a patient's eye.

BACKGROUND OF THE INVENTION (a) The Cornea, Its Diseases and Current Treatments:

The cornea is the clear cover of the eye and is also the main focusing lens in the eye. Disorders of the cornea, which adversely affect its shape or clarity, can cause loss of vision. Such disorders include Fuchs' endothelial dystrophy, pseudophakic bullous keratopathy, keratoconus, and herpes virus infection. When these conditions are severe the most common treatment is a full thickness corneal transplant which is also known as penetrating keratoplasty.

Penetrating keratoplasty is the removal of a full-thickness disk of diseased corneal tissue followed by the replacement of the diseased full-thickness disk of tissue by a full thickness disk of donated healthy corneal tissue. Currently, the diseased tissue is removed by the use of a non-automated or automated corneal trephine combined with manual excision using scalpels and or micro-surgical scissors. The disk of donated healthy corneal tissue is then secured to the recipient cornea by the means of sutures using micro-surgical techniques. Penetrating keratoplasty can provide dramatic improvements in vision in patients who have opacified or irregularly shaped corneas. Approximately, 40,000 corneal transplants are performed annually in the United States.

However, there are distinct disadvantages of penetrating keratoplasty. For example, penetrating keratoplasty has a long recovery time and typically takes between 6 to 12 months to achieve good vision. Moreover, because the donor corneal tissue is sutured manually, even in the hands of an experienced corneal surgeon, irregularities in the shape of the cornea frequently occur and can produce decreased vision because of induced astigmatism. The donated corneal tissue can also be rejected by the recipient's immune system with resulting loss of transparency of the donated cornea. Penetrating keratoplasty also has the potential for a devastating complication called expulsive suprachoroidal hemorrhage. In this complication, a spontaneous hemorrhage from the choroidal blood vessels behind the retina can occur during penetrating keratoplasty surgery after the diseased cornea has been removed and before the donor cornea has been sutured securely in place. Because the eye is open to atmospheric pressure in this situation, there is no normal intraocular pressure to stop the choroidal vessels from bleeding. The terrible result is that the retina, vitreous, and crystalline lens may be expulsed from the opening in the cornea resulting in blindness. This complication is estimated to occur approximately 1 in 500 cases with penetrating keratoplasty. Endophthalmitis (i.e. infection of the inside of the eye) is another serious complication that can occur and can also cause blindness if treatment is unsuccessful. Finally, after penetrating keratoplasty, the eye is very sensitive to injury, since the junction of the transplanted cornea and the recipient cornea can be easily disrupted with even mild trauma.

Because of the disadvantages of penetrating keratoplasty other methods of corneal surgery have recently been developed, as follows.

Lamellar keratoplasty is the general term for corneal surgeries that involve cutting within the layers (lamellae) of the cornea. Lamellar keratoplasty techniques allow removal and replacement of specific layers of the cornea. It is useful to be able to remove and transplant specific layers of the cornea because there are common corneal conditions that involve only certain layers of the cornea.

For example, a scar in the cornea from a herpes virus infection may affect only the superficial layers of the cornea. Removal and transplantation of the superficial layers of the cornea may be all that is necessary to restore sight to an eye that has a superficial scar and avoids many of the complications that can be associated with penetrating keratoplasty including endophthalmitis and expulsive suprachoroidal hemorrhage.

Another example would be Fuchs' endothelial dystrophy. The endothelium is the innermost layer of the cornea, which is responsible for pumping fluid out of the corneal tissues. This removal of fluid prevents the cornea from swelling and becoming opaque. In Fuchs' endothelial dystrophy, the endothelium is damaged and is unable to adequately pump fluid out of the cornea, which results in swelling and opacification of the cornea. Removal of the diseased inner layers of the cornea and transplantation with a layer of healthy tissue can restore clarity to the cornea and vision to the eye. By only exchanging the inner layers of tissue, the front surface of the cornea is essentially undisturbed. This decreases the likelihood of post-surgical astigmatism and may also result in less risk of rejection of the transplanted tissue.

A particular technique of lamellar keratoplasty is anterior lamellar keratoplasty. Anterior lamellar keratoplasty is a procedure where the superficial layers of the cornea are separated from the deeper layers with a hand held scalpel or an automated corneal surgical device called a microkeratome. Using this technique, a cap of the superficial layers of the cornea is removed and then replaced with a healthy cap from the superficial layers of the donor cornea.

Unfortunately, corneal tissue removal and replacement by the free hand method is extremely difficult to perform. Under the best of circumstances, it usually results in irregular astigmatism that is caused by irregularities in the thickness of the corneal tissue removed as well as in the thickness of the transplanted tissue. The irregular astigmatism typically limits the best spectacle corrected vision to no better than 20/40.

As stated above, automated anterior lamellar keratoplasty involves the excision of a cap of superficial corneal tissue by the use of a microkeratome. Similarly, the same apparatus can be used to prepare a cap of superficial donor corneal tissue for transplantation. The donor tissue is then sutured to the recipient cornea. The sutures are typically removed within the first few months to minimize astigmatism. Unfortunately, a problem that can occur with this technique is that the transplanted donor disk may be dislodged with relatively minor trauma, even after prolonged periods of time. This can occur because the cap of corneal tissue is only held in place by the relatively weak healing between the layers of donor and recipient tissue and there is no support against lateral or vertical pressure.

Another particular technique of lamellar keratoplasty is posterior lamellar keratoplasty. Posterior lamellar keratoplasty is a procedure where the deeper (i.e. rear) layers of the cornea are separated from the superficial layers with a hand held scalpel or an automated microkeratome. A disk of the deeper layers of the cornea is removed and then replaced with a healthy disk from the deeper layers of the donor cornea.

In the free hand posterior lamellar keratoplasty technique, a blade is manually used to create a pocket in the deep layers of the cornea. An internal manual trephine is then used to cut a disk of the deepest corneal layers. The disk of the deepest corneal layers is then excised with microsurgical scissors and or scalpels. A disk of the deepest corneal layers is then placed inside the manually created pocket to fill the space of the excised corneal tissue. The transplanted disk of tissue initially stays in place by the pumping mechanism of the corneal endothelial cells and then gradually heals into place permanently. One significant advantage of this technique is that post-operatively, the eye is much less susceptible to injury than in other methods of corneal transplantation. Moreover, because the transplantation occurs within a pocket of the corneal tissues, the transplant is well protected by the intact boundaries of the corneal pocket. Unfortunately, the main disadvantage of such free hand technique is that it is very difficult to manually create a pocket in the corneal tissues, wherein the pocket is of uniform depth. Rather, it is instead quite possible to either prematurely cut through the deepest layers of the cornea and thus enter the anterior chamber, or to accidentally cut too superficially and thus exit from the superficial cornea. Unfortunately, the inability to create a uniform pocket will necessitate the abandonment of posterior lamellar keratoplasty and will require conversion to traditional penetrating keratoplasty.

Using a motorized microkeratome for posterior lamellar keratoplasty involves the creation of a flap of corneal tissue with a motorized blade. This is followed by excision of a disk of the deepest layers of the cornea including the endothelium. The excised disk of corneal tissue (including the endothelium) is replaced by the same layers from a donor cornea. The donated corneal disk is then secured in place with sutures. The corneal flap of the recipient cornea is also secured with sutures for up to several months. A disadvantage of this technique is that, like penetrating keratoplasty, the inside of the eye is exposed to atmospheric pressure and therefore there is also a risk of suprachoroidal hemorrhage with this technique. Another disadvantage is that post-operatively the eye is still fairly vulnerable to injury. For example, even minor trauma could result in flap dislocation or rupture of the transplant-recipient junction.

Recently anterior lamellar keratoplasty and posterior lamellar keratoplasty have also been performed on an experimental basis where the incisions have been created with a laser. Two disadvantages of this technique are the high cost of lasers and potential difficulty for the laser to create incisions in corneas that are scarred or opacified. See U.S. Pat. No. 6,325,792 to Swinger et. al.

(b) Treatment of Ametropia:

Ametropia, the incorrect focusing of light rays onto the retina, is the most common cause of decreased vision in humans. Common examples of ametropia include myopia, hyperopia or hypermetropia, and astigmatism. Because the cornea is the primary focusing lens in the eye, modification of the shape of the cornea by surgery has the ability to cause dramatic improvements in vision in patients that have ametropia.

LASIK (laser assisted in situ keratomileusis) is a method of laser vision correction that can dramatically improve vision by changing the shape of the cornea to allow the proper focus of light rays onto the retina. In the LASIK technique, a motorized blade is used to cut away a thin flap of tissue from the front of the cornea. The flap of corneal tissue is then lifted to expose the interior surface of the cornea. This exposed interior surface is then reshaped by the application of laser light. The flap of corneal tissue is then repositioned over the reshaped interior portion of the cornea. The flap initially stays in position through the natural pumping mechanism of the corneal endothelial cells and then gradually heals into place permanently. In this procedure, there is considerable variability in the size and shape of the laser treatment. However, with current corneal surgical devices the size and shape of the flap that covers the laser treatment is unfortunately rather limited.

Another vision improvement technique is keratophakia. Keratophakia is the insertion of a lens within the cornea. Keratophakia can also modify the curvature of the cornea for the purpose of improving a patient's vision. In Keratophakia, a pocket is made within the corneal tissues usually by means of a hand held blade. U.S. Pat. Application 20010004702 to Peyman describes a non-motorized apparatus for creating such a pocket within the cornea. In the Peyman device, movement of the blade is created by manually twisting the blade. After the pocket is made within the corneal tissue, an organic or synthetic lens is implanted within the pocket to reshape the cornea in order to change the focus of light rays. The disadvantage of either a manual technique or a non-motorized technique is that the uniformity of the pocket is largely dependent on the surgeon's skill and experience and therefore there can be a high degree of variability.

Because of the apparent difficulties with the current corneal surgical devices there is still a continuing need for an improved apparatus and method to create a pocket, flap, or a cap of corneal tissue in a live or donor cornea, wherein the pocket, flap, or cap is of uniform depth and thickness.

SUMMARY OF THE INVENTION

In preferred aspects of the invention, the present invention provides a system for cutting the cornea of an eye, comprising: a moveable member with, a cutting blade at one end, a pivot element disposed thereon, and a cutting guide restraint disposed thereon; a mechanism for oscillating the moveable member around the pivot element; a cutting guide configured to engage the cutting guide restraint on the moveable member and thereby limit the degree of angular movement of the cutting blade as the moveable member oscillates about the pivot element; a positioning system configured to advance the moveable member with respect to the cutting guide such that the shape of the cutting guide determines the shape of a cut made by the cutting blade; a suction ring for stabilizing the cornea; and an applanating plate for flattening the cornea.

In preferred aspects of the invention, the present invention also provides a moveable member configured for use with a system for cutting the cornea of an eye, having: a cutting blade at one end; a pivot element disposed thereon; and a cutting guide restraint disposed thereon. Most preferably, such moveable member is disposable.

In preferred aspects of the invention, one or all of the following components: the moveable member, the cutting guide, the mechanism for oscillating the moveable member, and the suction ring, are disposable.

In preferred aspects, the shape of the cutting guide determines the shape of a cut made by the cutting blade by the cutting guide restraint contacting different portions of the cutting guide as the moveable member is advanced with respect to the cutting guide. For example, the cutting guide may simply comprise a hollow section. In this case, the cutting guide restraint moves back and forth within this hollow section with the cutting guide restraint on the moveable member contacting alternate sides of the hollow section. As such, the size of the arc through which the cutting blade moves is defined by the width of the hollow cutting guide as the cutting guide restraint on the moveable member is advanced along the length of the hollow cutting guide.

In preferred embodiments, the moveable member has a flexible transmission portion opposite to its cutting blade. A motorized linkage may be connected to the moveable member to cause it to pivot about its pivot point. In preferred aspects, the cutting blade at one end of the moveable member oscillates back an forth in an arc about the pivot element when an (opposite) end of the moveable member is moved back and forth by the motorized linkage.

In alternate preferred aspects, the mechanism for oscillating the moveable member around the pivot element may comprise any form of a mechanical, electrical, magnetic or pneumatic system, but the present invention is not so limited.

In alternate preferred aspects, the positioning system that moves the moveable member relative to the cutting guide may comprise any form of a mechanical, electrical, magnetic or pneumatic system, but the present invention is not so limited.

In preferred aspects of the invention, the present invention also provides a method of cutting a cornea, including: penetrating a cornea with a cutting blade at one end of a moveable member; oscillating the moveable member back and forth in an arcuate path about a pivot point thereon; and advancing the pivot point with respect to the cornea, thereby cutting the cornea with the cutting blade, while limiting motion of the cutting blade as the moveable member pivots about the pivot element by engaging a cutting guide restraint on the moveable member with a cutting guide such that the shape of the cutting guide determines the shape of the cut in the cornea.

In preferred aspects, the pivot point of the moveable member is advanced with respect to the cutting guide such that the cutting guide restraint of the moveable member contacts different portions of the cutting guide. In further preferred aspects, the cornea is stabilized with a suction ring; and the front surface of the cornea is flattened with an applanating plate prior to penetrating the cornea with the cutting blade.

In different embodiments, the applanating plate may be held at a fixed position as the cutting blade cuts through the cornea, or the applanating plate may be advanced across the cornea as the cutting blade cuts through the cornea.

Accordingly, the present invention provides a system and method of creating a pocket of uniform depth in the cornea. The pocket can be made of various shapes and sizes, between various layers of a live or donor cornea. The present invention also provides a system and method of creating a flap or cap of uniform thickness. The flap or cap can be made of various shapes and sizes from a live or donor cornea.

One advantage of the present system is that it is able to create a pocket of uniform depth within the cornea. Another advantage of the present system is that it is able to create a cut into the cornea wherein the cut has an external opening that is smaller than the internal dimensions of the pocket. Accordingly, the present invention may be used to transplant a portion of the inner layer of the cornea with the advantage that such transplantation may occur in a relatively closed system protected from atmospheric pressure. This advantageously reduces the risk of expulsive suprachoroidal hemorrhage. Additionally, having the external opening be smaller than the internal dimensions of the pocket will also make the eye much more resistant to trauma than would be the case in penetrating keratoplasty.

BRIEF DESCRIPTION OF THE DRAWINGS

FIG. 1 is a top plan view of the moveable member and associated cutting guide.

FIG. 2 is a side elevation view corresponding to FIG. 1.

DETAILED DESCRIPTION OF THE DRAWINGS

(a) Description of the Invention

In preferred aspects, the present invention provides a corneal surgery system that can be used to cut a live or donor cornea to form a pocket, flap or cap by separating the layers of the cornea. Specifically, the present invention provides a system for automatically creating a pocket of uniform depth, which can be of various shapes and sizes, between the layers of a live or donor cornea. The present invention may also be used to create a flap or cap of corneal tissue in a live or donor cornea.

In accordance with the present invention, a system for cutting a cornea is provided. The system comprises a cutting blade that is moved back and forth in an arcuate path while simultaneously being advanced to cut through a cornea. As will be explained, the degree of angular movement of the cutting blade is limited by contacts between a moveable member (to which the cutting blade is attached) and a cutting guide.

(b) Components of the Present Invention

Operation of the present invention can be understood by reference to FIGS. 1 to 5 which illustrate the movement of the moveable member with respect to the cutting guide.

FIGS. 6A to 7C and 9 and 10 show further details of various embodiments of the present invention.

Figure 8A:
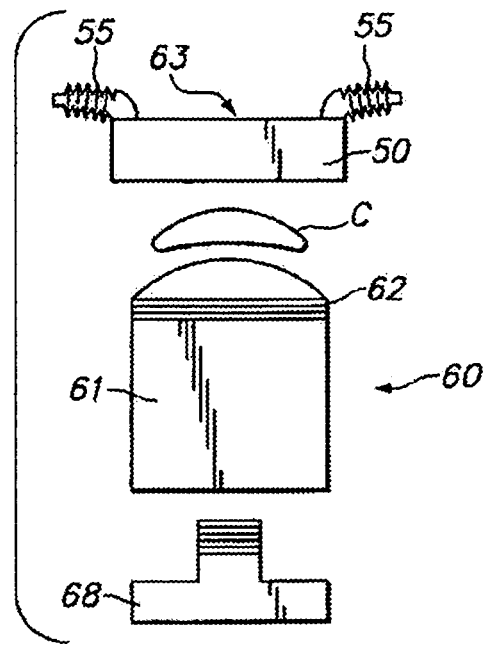
FIG. 8A is a side elevation view of an optional anterior chamber maintainer that may be affixed to the suction ring of the present invention.
Figure 8B:
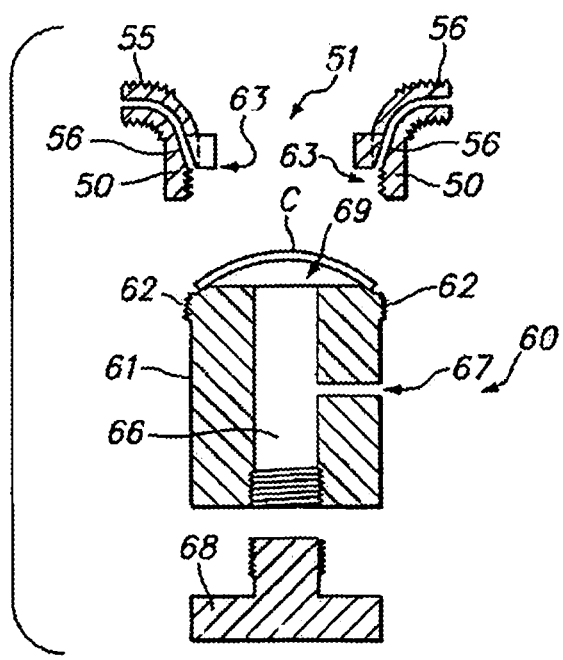
FIG. 8B is a sectional side elevation view corresponding to FIG. 8A, showing inner workings of the anterior chamber maintainer.

FIGS. 8A and 8B show an optional attachment device that can be used with various embodiments of the present invention.

Figure 11:
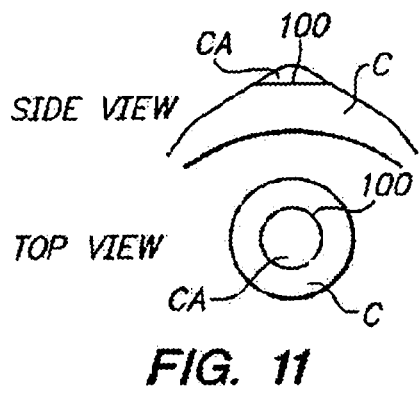
FIG. 11 is corresponding side and top views of anterior lamellar keratoplasty procedure performed with prior art techniques.
Figure 12:
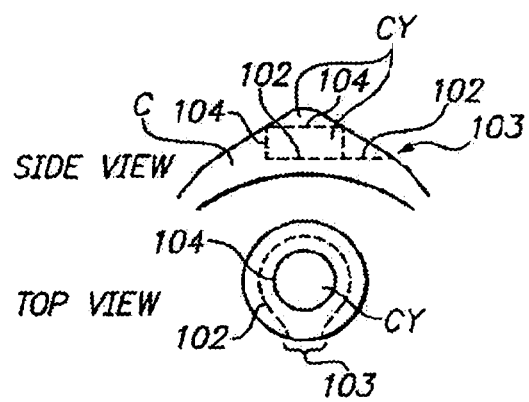
FIG. 12 is corresponding side and top views of anterior lamellar keratoplasty procedure performed with a technique in accordance with the present invention.
Figure 13:
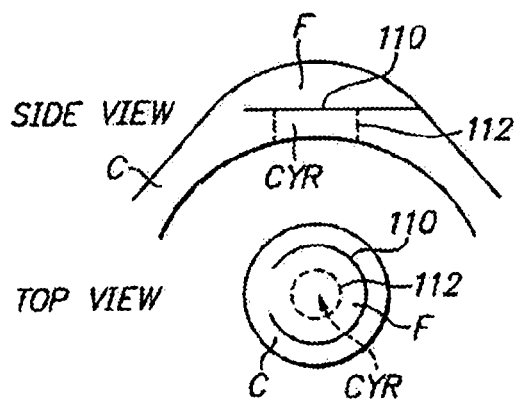
FIG. 13 is corresponding side and top views of a posterior keratoplasty procedure performed with prior art techniques.
Figure 14:
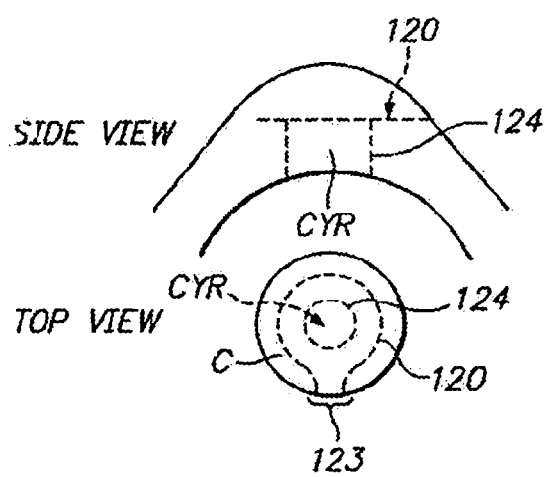
FIG. 14 is corresponding side and top views of a posterior keratoplasty procedure performed with a technique in accordance with the present invention.

Lastly, FIGS. 11 and 13 show surgical cutting procedures performed by pre-existing techniques. FIGS. 12 and 14 show comparable surgical cutting procedures performed with the system of the present invention.

Referring first to FIGS. 1 and 2, a moveable member 10 is provided. Moveable member 10 has a cutting blade 12 at one end. In optional aspects, cutting blade 12 may be made of steel, stainless steel, sapphire, diamond, plastic or ceramic, but is not so limited. Rather, any material suitable for cutting the cornea may be used. Moveable member 10 has a pivot 14 thereon. As will be shown, moveable member 10 is oscillated such that it sweeps back and forth in an angular path of direction 0 about its pivot 14. Moveable member 10 further includes a cutting guide restraint 16 projecting therefrom. Cutting guide restraint 16 is received with a hole 22 of a cutting guide 20.

Figure 4:
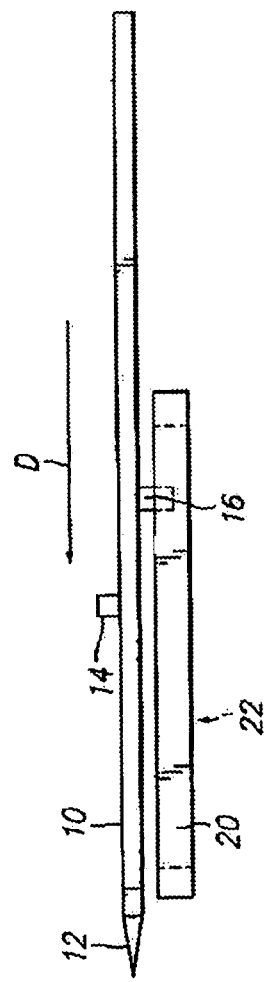
FIG. 4 is a side elevation view corresponding to FIG. 3.

As shown in FIGS. 2 and 4, cutting guide restraint 16 projects from the bottom of moveable member 10 and cutting guide 20 is positioned below moveable member 10. The present invention is not so limited. Alternate embodiments are possible, all keeping within the scope of the present invention. For example, cutting guide restraint 16 may instead project from the top of the moveable member with cutting guide 20 being placed above moveable member 10. Other designs are also possible.

In accordance with the present invention, corneal cutting is performed by angular back and forth movement (i.e.: oscillation in direction 0) of moveable member 10 about pivot 14 at the same time that pivot 14 is advanced in direction D with respect to cutting guide 20. As moveable member 10 is advanced in direction D, cutting guide restraint 16 will contact successive locations around the sides of hole 22 in cutting guide 20. The novel shape of hole 22 in cutting guide 20 will have the effect of limiting the degree of angular (i.e.: side to side) motion of cutting blade 12. Accordingly, as cutting blade 12 is advanced in direction D with respect to cutting guide 20 (by advancing pivot 14 of moveable member 10 in direction D), the novel shape of hole 20 will cause cutting blade 12 to cut a preferred shape of cut in the cornea.

Figure 3:
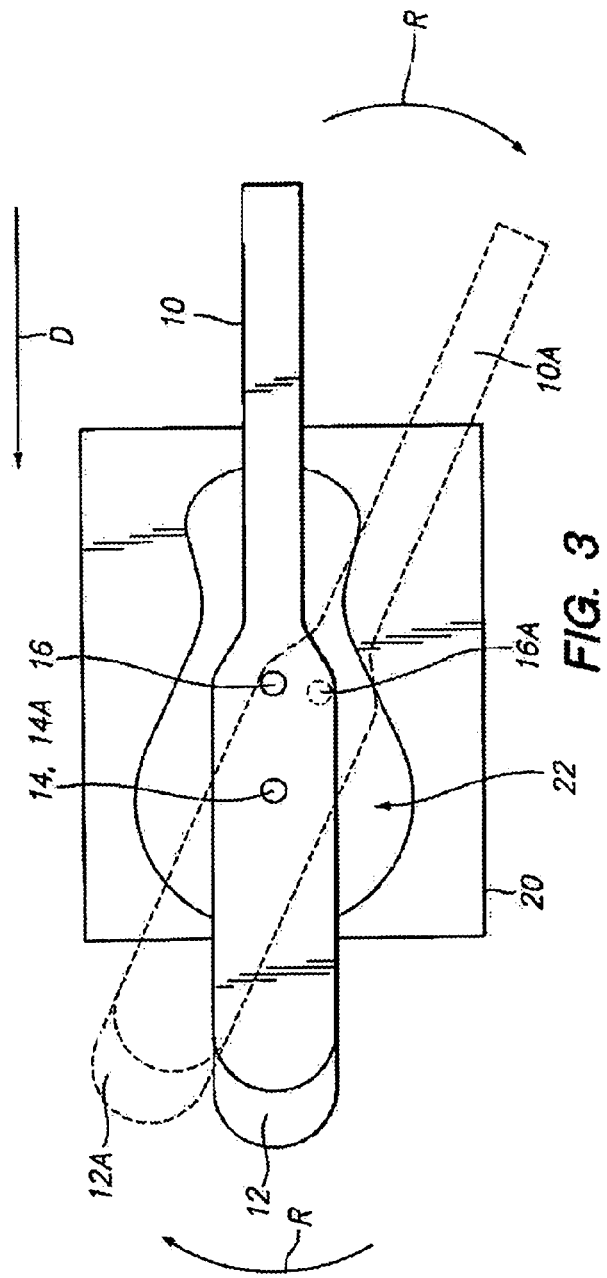
FIG. 3 is a view similar to FIG. 1, but additionally showing (in dotted lines) the moveable member moved to a second position at which a cutting guide restraint on the moveable member contacts a side of the cutting guide.

This can be seen as follows. Referring to FIG. 3, moveable member 10 is rotated in direction R about pivot 14 to the position shown in dotted lines as 10A. At such location, cutting guide restraint reaches the position shown in dotted lines as 16A (at which time it contacts the side of hole 22, as shown). Blade 12 is thus not able to rotate further in direction R than to the position shown in dotted lines as 12A. Thereafter, moveable member 10 will be rotated in the opposite direction such that cutting guide restraint 16 will instead contact the opposite side of hole 22 (thus limiting maximum angular movement in the opposite direction).

Concurrently, moveable member 10 will be moved in direction D with respect to cutting guide 20. This movement is shown by referring first to FIG. 4 and then to FIG. 2. (FIG. 4 shows the position of the moveable member with respect to the cutting guide when cutting is first commenced, and FIG. 2 shows the position of the moveable member with respect to the cutting guide after cutting has been carried out for some time).

Figure 5A:
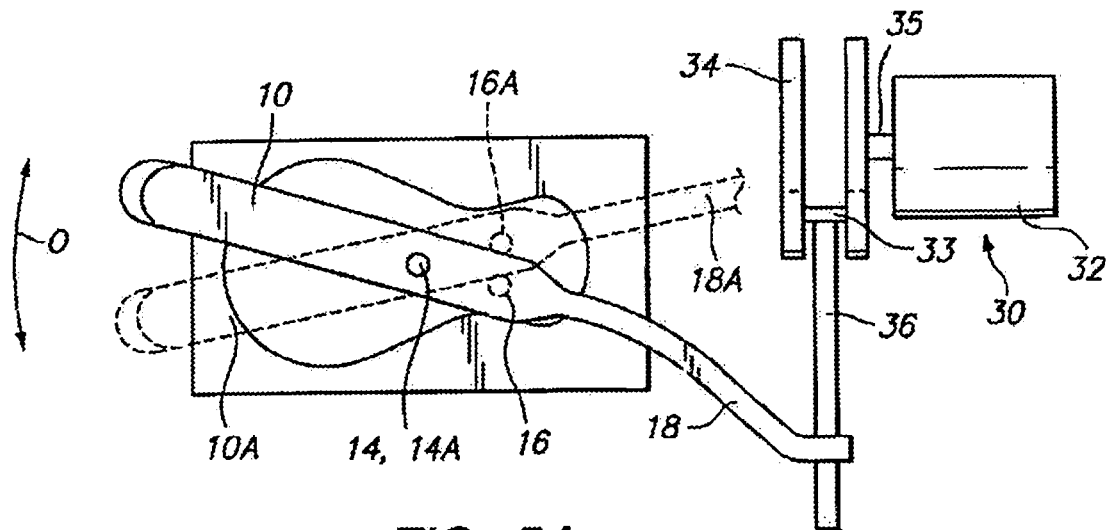
FIG. 5A is a top plan view showing the moveable member moved from a first position at which the cutting guide restraint contacts one side of the cutting guide (shown in solid lines) to a second position at which the cutting guide restraint contacts the other side of the cutting guide (showing in dotted lines).

FIG. 5A illustrates a mechanical system for oscillating moveable member 10 back and forth in direction 0. Specifically, FIG. 5A shows moveable member 10 at a first maximum angular extension (shown in solid lines) and moveable member 10 at an opposite maximum angular extension (shown in dotted lines). In preferred aspects of the invention, moveable member 10 includes a flexible portion 18. Flexible portion 18 may optionally comprise a spring or a flexible piece of plastic or rubber. As can be seen, an advantage of having portion 18 flexible is that it bends when cutting guide restraint 16 is stopped from further angular movement by its contact with the sides of hole 22. A system 30 for oscillating moveable member 10 may include a motorized mechanical linkage for rotating moveable member 10 back and forth by alternatingly moving flexible portion 18 back and forth in a direction generally perpendicular to direction D. For example, system 30 may include a motor 32 that rotates a wheel 34 (by rotating shaft 35). A pin 33 is eccentrically mounted to wheel 34 such that as wheel 34 rotates, the movement of pin 33 causes link 36 to move back and forth, thereby repetitively moving moveable member 10 back and forth between positions (shown as 10 and 10A).

Figure 5B:
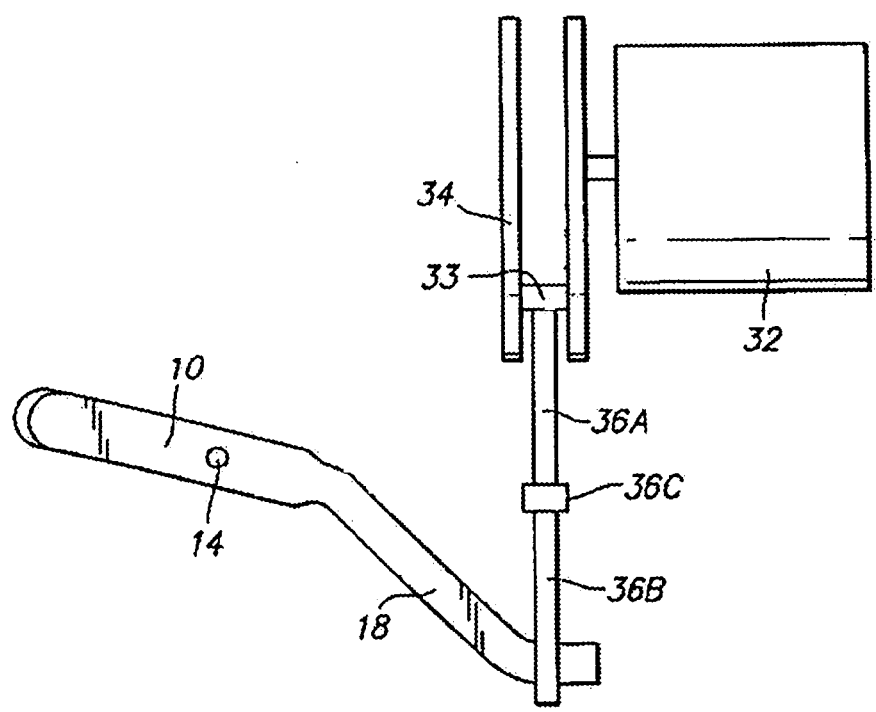
FIG. 5B is a top plan view showing the linkage of the moveable member to a motor as consisting of two links connected by a joint.
Figure 5C:
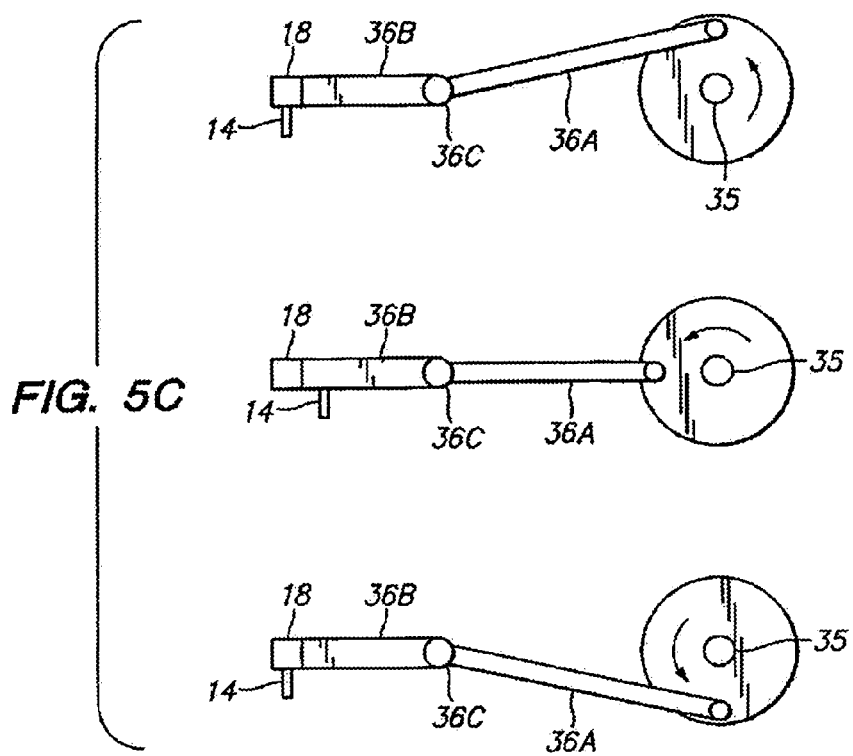
FIG. 5C is a schematic side elevation view showing that the presence of two sequential links connected by a joint can minimize vertical up and down motion of the moveable member.

In preferred aspects, link 36 may include more than one link member connected together in series. An advantage of having link 36 include more than one link member is that this can minimize up and down movement of the flexible portion 18 and moveable member 10 as pin 33 moves around shaft 35. FIG. 5B shows link 36 consisting of portions 36A, 36B, and 36C. Portion 36C is a joint which connects portion 36A and 36B. FIG. 5C shows how joint 36C allows portion 36A to move in a vertical up and down motion while portion 36B moves predominantly in a transverse horizontal motion relative to pivot 14. Portion 36B, therefore transmits predominantly horizontal back and forth motion to flexible portion 18 and moveable member 10 around pivot 14 and minimizes up and down motion.

As can be seen in FIGS. 1, 3 and 5, hole 22 in cutting guide has a novel shape. In particular, hole 22 has a "gourd" or a "bowling pin" shape. The present inventor has determined that such "gourd" or a "bowling pin" shaped hole will result in a corneal cut that is roughly shaped like an "ice cream cone" (i.e. a triangular section with a convexly-curved end). Preferably, hole 22 will have a symmetrical shape. As will be shown, a particular advantage of this shape of cut is that it will create a pocket in the cornea wherein the opening through the surface of the cornea is smaller in width than the internal dimensions of the pocket.

In accordance with the present invention, an applanating plate is positioned against the front surface the cornea and the intraocular pressure is elevated by a suction ring during the time the cornea is cut by the movement of the cutting blade. The applanating plate presses down against the front surface of the cornea and the intraocular pressure presses up against the back surface of the cornea, thereby uniformly flattening a portion of the cornea. This has the advantage of ensuring a uniform thickness of the cornea is cut by the cutting blade when forming a pocket, flap, or cap.

Figure 6A:
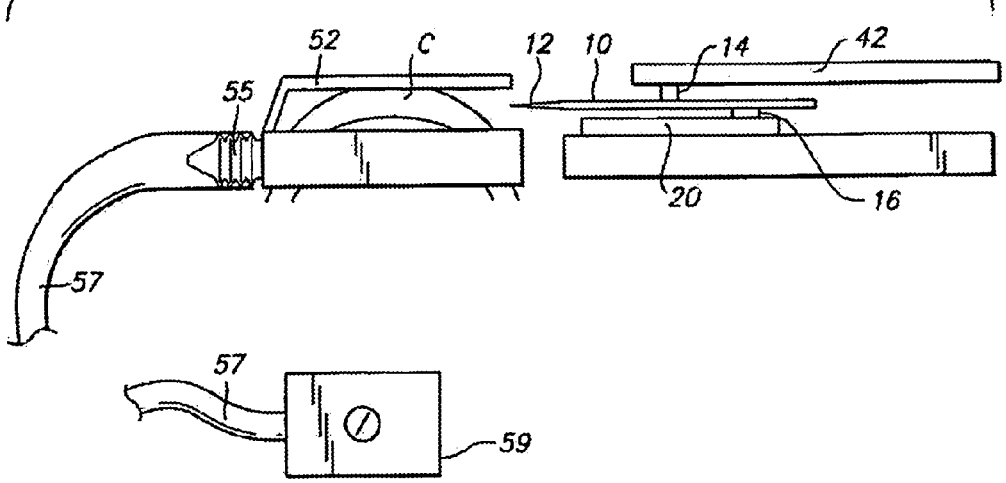
FIG. 6A is a schematic side elevation view of an embodiment of the invention in which a non-moving applanating plate flattens the surface of the cornea prior to cutting.
Figure 6B:
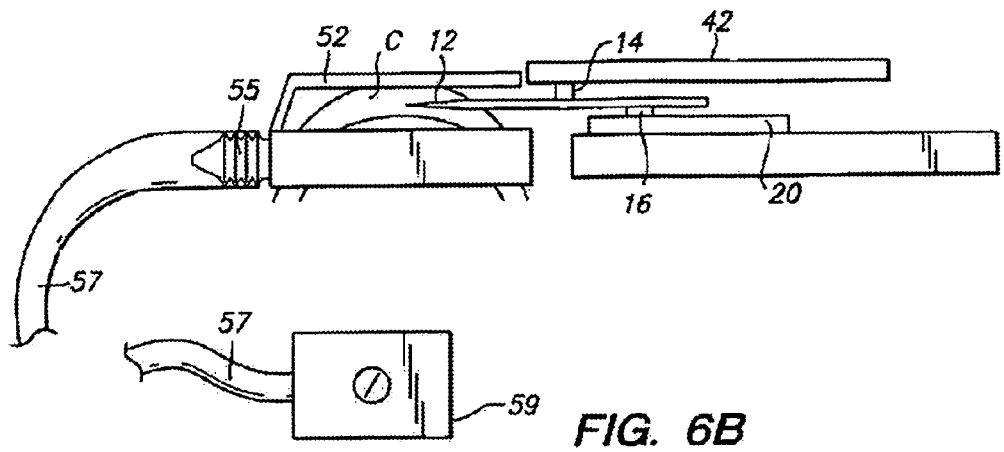
FIG. 6B is a schematic side elevation view of an embodiment of the invention in which a non-moving applanating plate flattens the surface of the cornea during cutting.
Figure 7A:
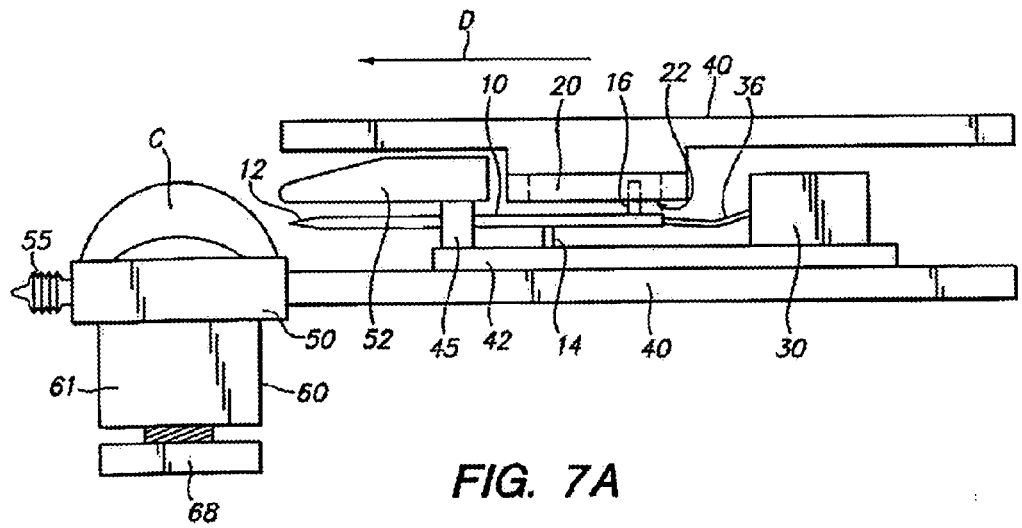
FIGS. 7A and 7B are sequential schematic side elevation views of an embodiment of the invention in which an applanating plate advances across the surface of the cornea simultaneously with the cutting blade cutting through the cornea.
Figure 7B:
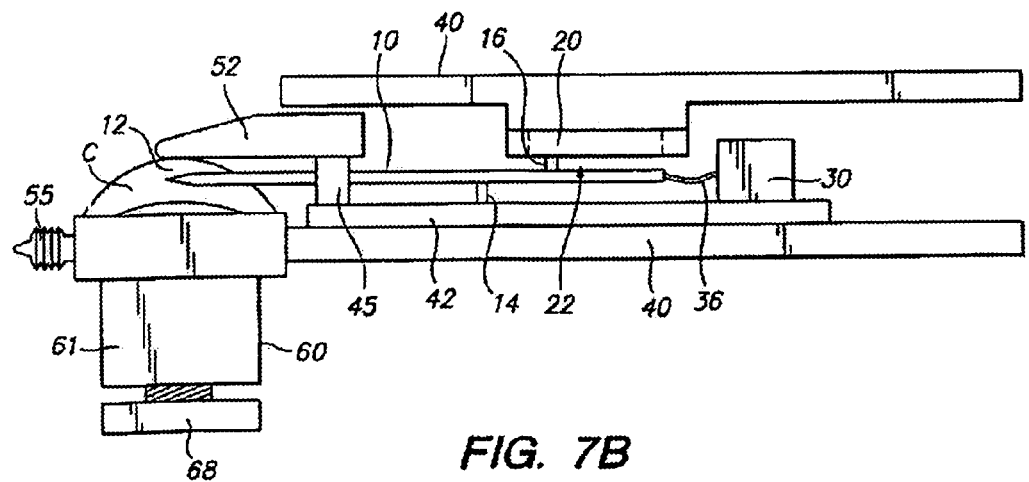
Figure 7C:
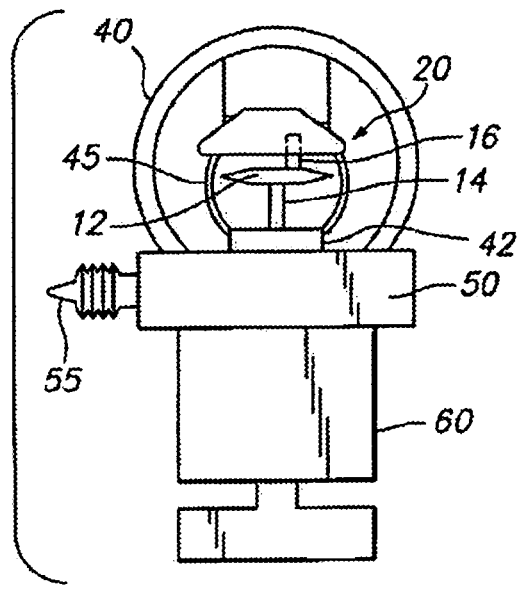
FIG. 7C is a front elevation view of the embodiment of the invention shown in FIGS. 7A and 7B.

In one embodiment, the applanating plate is positioned at a fixed location on the surface of the cornea prior to commencing cutting of the cornea with the cutting blade. An example of such system is shown in FIGS. 6A and 6B. In an alternate embodiment of the invention, the applanating plate is advanced over the surface of the cornea concurrently with the cutting blade penetrating and cutting across the cornea. An example of such system is shown in FIGS. 7A to 7C. Additionally, FIGS. 7A to 7C show an optional anterior chamber maintainer 60 which is especially useful when cutting a donor cornea. It is to be understood that anterior chamber maintainer 60 is an optional attachment that may or may not be used with the various embodiments of the invention shown in FIGS. 6A to 7C, as desired.

Referring first to FIG. 6A, when vacuum pump 59 connected to suction ring 50 by tubing 57 via tubing connector 55, creates a vacuum to a predetermined level, suction ring 50 holds cornea C (positioned therearound) in a fixed position. The vacuum transmitted by suction ring 50 also raises the pressure against the rearward surface of cornea C because the vacuum causes the eyeball to partially squeeze into the suction ring. The applanting plate 52 pushes down against the front surface of the cornea, thereby flattening the cornea. As illustrated, a member 42 is used to advance pivot 14 in direction D from the position shown in FIG. 6A to the position shown in FIG. 6B. (The relative movement of cutting guide restraint 16 within cutting guide 20 can be seen). In accordance with the present invention, member 42 may include any form of mechanical linkage, guide rails or even simply a portion of the housing of the device.

FIGS. 7A to 7C show an alternate embodiment of the invention in which applanting plate 52 is moved across cornea C concurrently with blade 12 advancing (i.e. cutting through the cornea) in direction D. Moveable member 10, cutting guide 20 and system 30 are all positioned inside housing 40. As was explained above, system 30 causes moveable member 10 to rotate back and forth around pivot 14, with cutting guide restraint 16 is received within cutting guide 20. (In contrast to the embodiment of FIGS. 6A and 6B; however, pivot 14 instead projects from the bottom of moveable member 10, and cutting guide 20 is positioned above moveable member 10). Member 42 is advanced in direction D within housing 40, thereby moving moveable member 10 in direction D. Cutting guide 20 is connected to housing 40 such that cutting guide restraint 16 moves along through hole 22 therein. Further details can be seen in FIG. 7C in which supports 45 hold applanating plate 52 within housing 40 such that moveable member 10 is free to move side-to-side therebetween.

FIGS. 7A and 7B show an optional anterior chamber maintainer 60 that may be used as an attachment to the present invention. Further details of the anterior chamber maintainer 60 are shown in FIGS. 8A and 8B. Anterior chamber maintainer 60 is specifically used when cutting tissue in a donor cornea. The donor corneal tissue is usually provided to the surgeon in the form of an excised cornea with a small rim of surrounding scleral tissue. As stated above, the present invention is designed to cut the cornea of a living complete eyeball. However, it is also necessary to have an attachment that will also enable the invention to cut a donated cornea that has been excised from the donor eyeball.

In accordance with the present invention, an optional anterior chamber maintainer 60 is provided to hold a donor cornea stable after the donor cornea has been cut away from the donor eyeball. As shown in the exploded view of FIGS. 8A and 8B, a cut away donor cornea C is placed on top of anterior chamber maintainer 60. In this preferred embodiment, suction ring 50 has an inner threading 63. The body of the anterior chamber maintainer 61 has an outer threading 62. The outer threading 62 is received into the inner threading 63 of suction ring 50. The inner threading 63 of suction ring 50 connects to outer threading of body 61, thereby firmly holding cornea C in place by trapping cornea C between suction ring 50 and body 61. The front surface of the cornea protrudes through the opening 51 of the suction ring. The body 61 has an interior chamber 66 that is filled with fluid or gas. A bottom portion 68 screws into the bottom end of interior chamber 66. By rotating bottom portion 68, the volume of interior chamber 66 can be adjusted. The top end 69 of fluid chamber 66 is open such that the fluid or gas within interior chamber 66 provides pressure against the rear surface of the donor cornea C. By providing pressure against the rear surface of donor cornea C, anterior chamber maintainer 60 simulates the pressures that would exist behind cornea C in a living eyeball. Moreover, the pressures produced in interior chamber 66 applied to the rear surface of cornea C allows the donor corneal tissue to be pressed flat against applanating plate 52 so that a cut of uniform depth can be made by blade 12. The amount of pressure inside the interior chamber may be measured by a pressure gauge or sensor connected to opening 67.

FIGS. 8A and 8B illustrate the tubing connector 55 on the top surface of the suction ring 50. This is an alternate location for tubing connector 55. In FIGS. 6A, 6B, 7A, 7B, and 9 the tubing connector 55 is shown on the side surface of the suction ring 50. FIG. 8B illustrates that there is a hollow space 56 inside tubing connector 55 which communicates with the inside of suction ring 50 that allows the vacuum pump 59 to generate vacuum inside suction ring 50. Advantageously, the generation of vacuum by vacuum pump 59 is not necessary for a cut to be made in the donor cornea C, because the cornea is already fixed in position by the anterior chamber maintainer 60 and the pressure on the rear surface of the cornea can also be sufficiently elevated by the anterior chamber maintainer 60.

Figure 9:
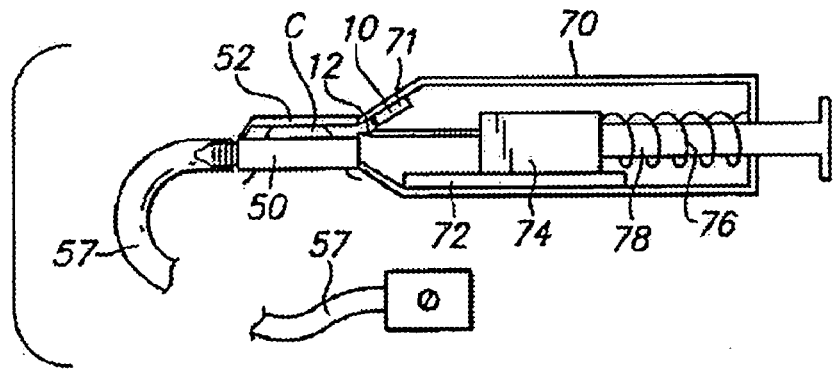
FIG. 9 is a sectional side elevation view of an embodiment of the invention in which an operator manually depresses a plunger to advance the cutting blade.

FIG. 9 shows another embodiment of the present invention in which the cutting blade is manually advanced by an operator. Within housing 70 are provided a guide rail or track 72 along which a cutting mechanism 74 moves. Cutting mechanism 74 may be a self-contained unit that includes moveable member 10, cutting guide restraint 16, a system for oscillating moveable member 10 about a pivot 14 thereon. A plunger 78 is connected to cutting mechanism 74. A spring 76 is connected at one end to housing 70 and at the other end to cutting mechanism 74. Spring 76 is a tension spring that tends to move cutting mechanism 74 so that blade 12 is retracted (as shown). When the operator depresses plunger 78, spring 76 will lengthen, and cutting mechanism 74 will move forward along track 72 such that blade 12 on moveable member 10 will advance between applanating plate 52 and suction ring 50, cutting through the cornea C. The interaction of cutting guide restraint 16 and cutting guide 20 will cause the cut to be of a preferred shape as was described above. Spring 76 will provide resistance to the forward motion of cutting mechanism 74 along track 72, thus limiting uncontrolled forward motion of moveable member 10's cutting blade 12. Optionally, a liquid dispensing system 71 to spray fluid to cool the cutting blade and the cornea during cutting. Such a liquid dispensing system may be incorporated into any of the various other embodiments of the invention, as desired.

Figure 10:
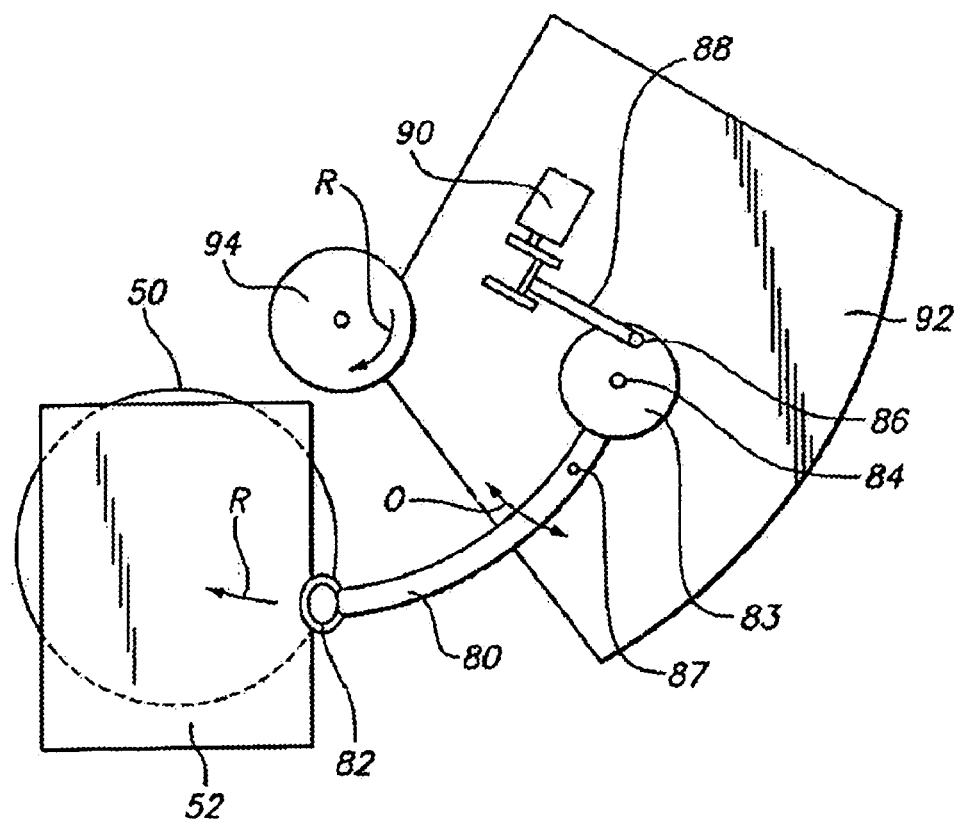
FIG. 10 is a top plan view of an embodiment of the invention in which the cutting blade is advanced through a curved path into the cornea.

FIG. 10 illustrates yet another embodiment of the invention in which a blade holder 80 having a blade 82 at one end is connected to moveable member 83 which pivots about a pivot point 84. As shown herein, blade 82 may be wider than the bladeholder 80, if desired. (Similarly, blade 12 may be wider than moveable member 10 in FIG. 1, if desired). A motor 90 moves a linkage 88 back and forth. Linkage 88 is connected to moveable member 83 by flexible member 86 such that moveable member 83 is made to oscillate back and forth about pivot point 84. Thus, blade holder 80 and blade 82 oscillates back and forth in direction O. Blade holder 80 has a cutting guide restraint 87 disposed thereon. Cutting guide restraint 87 mates with a cutting guide (not shown) the shape of which limits maximum angular movement of blade 82, in the manner previously described above. The various components of the invention are mounted to a plate 92 that is connected to a rotatable member 94 that is rotated in direction R such that plate 92 is moved in direction R such that blade 82 and blade holder 80 will advance between applanating plate 52 (thereabove) and suction ring 50 (therebelow) to cut the flattened cornea.

As illustrated in various figures herein, pivot 14 and cutting guide restraint 16 may each comprise protrusions extending from moveable member 10. Moreover, in various figures herein, cutting guide 20 is illustrated as comprising a hole 22. The present invention is not so limited. For example, the pivot 14 on moveable member 10 may instead comprise a hole dimensioned to receive a protrusion therein. Moreover, the cutting guide restraint may instead comprise a slot with the cutting guide comprising some form of protrusion interacting therewith.

(c) Method of Using the Present Invention for Transplanting Front or Rear Portions of a Donor Cornea As stated above, the present invention may be used to for cutting a cornea on a living patient, or for cutting a donor cornea. Due to the accuracy of the present invention's system of cutting, the present invention may be used for removing diseased or damaged sections of a living patient's cornea, and then replacing these sections with similar shaped sections cut from a donor cornea.

In various aspects of performing the method of the present invention, the "section" of the cornea that is transplanted may be the front portion or the rear portion of the cornea. Cutting away a section of the front of the cornea and replacing the excised section with a donor graft is known as "anterior lamellar keratoplasty". Cutting away a section of the rear of the cornea and replacing the excised section with a donor graft is known as "posterior lamellar keratoplasty".

FIG. 11 illustrates an anterior lamellar keratoplasty procedure performed with prior art techniques; and FIG. 12 illustrates an anterior lamellar keratoplasty procedure performed with a technique in accordance with the present invention. FIG. 13 illustrates an internal keratoplasty procedure performed with prior art techniques; and FIG. 14 illustrates a posterior lamellar keratoplasty procedure performed with a technique in accordance with the present invention. In each of FIGS. 11 to 14, a cut passing through the exterior of the cornea is shown in solid lines and a cut passing only through the interior of the cornea is shown in dotted lines.

Turning first to FIG. 11, a standard anterior lamellar keratoplasty procedure is shown. Specifically, a cut 100 is made through cornea C such that a frontal "cap" CA of tissue is removed for transplantation. A disadvantage of transplanting a frontal cap CA formed by cut 100 is that it s rather fragile, and prone to dislocation after surgery.

By instead using the present invention to form a cut 102 (FIG. 12), a pocket can be made in the cornea. A particular advantage of forming a pocket by cut 102 is that the pocket will have an opening 103 that is smaller than the interior width of the pocket. After the cutting blade forms cut 102, a trephine can be used to cut straight downwards into cornea in a cylindrical shaped cut 104. When cut 104 reaches cut 102, a cylindrical shaped portion CY of the cornea will be formed. This cylindrical shaped portion CY of the cornea of the donor cornea can then be transplanted into a similar cylindrical shaped hole cut into the living patient's cornea. A particular advantage of transplanting such a cylindrical shaped section (as opposed to transplanting a simple cap CA as shown in FIG. 11) is that a cylindrical shaped cornea section received into a cylindrical shaped hole will be much more stable and resistant to injury. Specifically, the donated corneal tissue would be much less likely to dislocate with vertical or lateral pressure following transplantation. After healing, the donor recipient disk would be much more resistant to vertical and or lateral displacement from mild trauma than superficial corneal tissue transplanted without the physical support of a rim of surrounding recipient corneal tissue.

Turning to FIG. 13, a standard posterior lamellar keratoplasty procedure is shown. A cut 110 is made in cornea C, as shown. Cut 110 does not pass fully across the cornea. Rather, a flap F of corneal tissue is formed by cut 110. After flap F is pulled back, a trephine or trephine section is then used to cut straight downwards, thus cutting a circular shaped cut 112 forming a cylindrical shaped portion CYR of the rear of the cornea.

By instead using the present invention to form a cut 120, (FIG. 14) a pocket can be made in the cornea. A particular advantage of forming a pocket by cut 120 is that the pocket will have an opening 123 that is smaller than the interior width of the pocket. After the cutting blade forms cut 120, a thin profile trephine (preferably mounted on a ring) or microsurgical scissors can be used to cut straight downwards into the deep layers of the cornea in a cylindrical shaped cut 124, thus forming a cylindrical shaped portion CYR of the rear of the cornea. An advantage of performing the operation in this manner is that it is not necessary to form and pull back a "flap" of tissue from the front of the cornea. Instead, the entire operation is performed without a large portion of the cornea being "open" to the external environment. Rather, the only opening into the cornea is through opening 123. This dramatically reduces the possibility for suprachoroidal hemorrhages.

In preferred aspects of the resent invention, openings 103 or 123 have a width of about 4 or 5 mm and interior pockets 102 and 120 have a maximum internal diameter of about 9 or 10 mm. Cylindrical corneal sections CY and CYR typically are about 7 to 8 mm in diameter in the patient's eye, and about 7 to 8 mm in diameter in the donor cornea.

In various aspects, the portion CYR of the donor cornea can be completely excised with the use of microsurgical scalpels and or scissors, and portion CY can be manually separated from the superficial layers of the cornea using microsurgical forceps.

In various aspects, viscoelastic can be injected onto the inside surface (relative to the center of the eyeball) of the CYR portion of the donor cornea to protect the corneal endothelium. The inner layer of the cornea is then partly folded in half with microsurgical forceps, with a cushion of viscoelastic preventing the endothelium on each half of the donor disk CYR from touching together. Viscoelastic can also be used to position the donor corneal disk into the space previously occupied by the excised recipient corneal disk CYR.

The opening 103 or 123 of the corneal pocket may optionally be closed with sutures or tissue glue to make the wound water tight. Possible tissue glues which could be used include cyanoacrylate, fibrinogen tissue adhesives, or dendrimers. Viscoelastic can be removed from the anterior chamber using irrigation of balanced salt solution and aspiration.

It is to be understood that the dimensions for the size and shape of cuts made in the recipient and donor corneal tissues are merely representative of the type of surgery which can be done. Thus, variations in the dimensions and shape of the pocket, flap, cap, and corneal donor or recipient disks are expected, all keeping within the scope of the present invention.

What is claimed is:

1. A method of cutting a pocket in a cornea, comprising:
   penetrating a cornea in a longitudinal direction through an opening with a cutting blade at one end of a moveable member;
   oscillating the moveable member back and forth in an arcuate path about a pivot point thereon; and
   advancing the pivot point longitudinally with respect to the cornea, thereby cutting the cornea with the cutting blade, while limiting motion of the cutting blade as the moveable member pivots about the pivot element by engaging a cutting guide restraint on the moveable member with a cutting guide along longitudinally successive locations on the cutting guide such that the shape of the cutting guide creates a pocket in the cornea, said pocket having a width greater than that of the opening and an area defined by the shape of the cutting guide.

2. The method of claim 1, wherein oscillating the moveable member back and forth in an arcuate path about the pivot point comprises:
   moving a portion of the moveable member opposite to the cutting blade back and forth with a motorized linkage.

3. The method of claim 1, wherein the pivot point of the moveable member is advanced with respect to the cutting guide such that the cutting guide restraint of the moveable member contacts different portions of the cutting guide.

4. The method of claim 1, further comprising:
   stabilizing the cornea with a suction ring; and flattening the cornea with an applanating plate prior to penetrating the cornea with the cutting blade.

5. The method of claim 4, wherein the applanating plate is held at a fixed position as the cutting blade cuts through the cornea.

6. The method of claim 4, wherein the applanating plate is advanced across the cornea as the cutting blade cuts through the cornea.

7. The method of claim 1, further comprising: cutting into a forward surface of the eye with a trephine.

8. The method of claim 1, further comprising:
   inserting a trephine section into a pocket created by the blade within the cornea; and cutting into a rearward surface with a trephine section.

9. The method of claim 1, wherein a portion of the cut in the cornea is conical in shape, and wherein a portion of the cut in the cornea is rounded in shape.

10. The method of claim 1, wherein the pivot point is advanced in a linear path.

11. The method of claim 1, wherein the pivot point is advanced in an arcuate path.

* * * * *